United States Patent [19]

Horide et al.

[11] 4,283,222
[45] Aug. 11, 1981

[54] EMULSIFIABLE CONCENTRATE FOR WEED CONTROL

[75] Inventors: Fumio Horide, Osaka; Kozo Tsuji, Fukazawahonmachi, both of Japan

[73] Assignee: Sumitomo Chemical Company, Limited, Osaka, Japan

[21] Appl. No.: 151,576

[22] Filed: May 20, 1980

Related U.S. Application Data

[63] Continuation-in-part of Ser. No. 67,457, Aug. 17, 1979, abandoned.

[30] Foreign Application Priority Data

Aug. 29, 1978 [JP] Japan ................................. 53-106107
Aug. 28, 1979 [BR] Brazil ................................. 7905536

[51] Int. Cl.³ ............................................. A01N 47/30
[52] U.S. Cl. .................................... 71/120; 71/DIG. 1
[58] Field of Search ............................ 71/120, DIG. 1

[56] References Cited

U.S. PATENT DOCUMENTS

| 3,119,682 | 1/1964 | Martin et al. | 71/122 |
| 3,373,010 | 3/1968 | Olson | 71/120 |
| 3,869,276 | 3/1975 | Priola et al. | 71/DIG. 1 |
| 4,129,436 | 12/1978 | Takemoto et al. | 71/120 |
| 4,174,960 | 11/1979 | Hendriksen | 71/DIG. 1 |

Primary Examiner—Donald G. Daus
Assistant Examiner—M. C. Eakin
Attorney, Agent, or Firm—Birch, Stewart, Kolasch & Birch

[57] ABSTRACT

An emulsifiable concentrate for weed control, which comprises 10 to 20 parts by weight of N'-[4-(4-methylphenethyloxy)phenyl]-N-methoxy-N-methylurea, 5 to 15 parts by weight of an emulsifier, 10 to 70 parts by weight of at least one of aromatic hydrocarbon solvents of the formula:

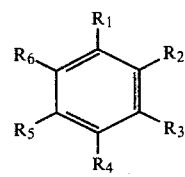

wherein $R_1$, $R_2$, $R_3$, $R_4$, $R_5$ and $R_6$ are each hydrogen or alkyl having 1 to 3 carbon atoms and 15 to 75 parts by weight of at least one of ketonic solvents having not more than 9 carbon atoms, of which the water solubility is not more than 10% by weight at room temperature.

6 Claims, No Drawings

EMULSIFIABLE CONCENTRATE FOR WEED CONTROL

This is a continuation-in-part application of our co-pending application Ser. No. 67,457, now abandoned, filed on Aug. 17, 1979.

The present invention relates to an emulsifiable concentrate for weed control. More particularly, it relates to an emulsifiable concentrate for weed control comprising as an active ingredient N'-[4-(4-methylphenethyloxy)phenyl]-N-methoxy-N-methylurea (hereinafter referred to as "Compound A").

The purpose of this invention is to provide an emulsifiable concentrate comprising Compound A in a high concentration, which has a good emulsion stability and an excellent storage stability at low temperatures. For instance, the emulsifiable concentrate of the invention does not produce any precipitation of the crystals of Compound A even after storage at 0° C. for 7 days.

Compound A is known to be a herbicide for treatment of soil and foliage, which shows a strong herbicidal activity against a wide variety of weeds and has a selectivity to soybean, rice, corn, peanut, cotton, wheat, etc. (cf. U.S. Pat. No. 4,129,436). Thus, Compound A exerts a strong herbicidal action at a small dose on broad-leaved weeds such as redroot pigweed (*Amaranthus retroflexus*), common lambsquarters (*Chenopodium alubum*), cocklebur (*Xanthium pennsylvanicum*), annual morningglory (*Ipomoea purpurea*), chickweed (*Stellaria media*), radish (*Raphanus sativus*), pale smartweed (*Polygonum lapathifolium*), toothcup (*Rotala indica*), pickerelweed (*Monochoria vaginalis*), false pimpernel (*Linderna pyxidaria*), pitchfork (*Bidens frondosa*), black nightshade (*Solanum nigrum*), sunflower (*Helianthus annus*), jimson weed (*Datura stramonium*) and velvetleaf (*Abutilon theophrasti*), Gramineae weeds such as goose grass (*Eleusine indica*), large crabgrass (*Digitaria sanguinalis*), barnyard grass (*Echinochloa crus-galli*), green foxtail (*Setaria viridis*) and nutsedge (*Cyperus difformis*), etc.

Compound A is usually employed in the form of emulsifiable concentrate or wettable powder. In general, an emulsifiable concentrate is preferred, because the use of Compound A in an emulsifiable concentrate produces a higher herbicidal activity than the use in a wettable powder, particularly when Gramineae weeds are treated. Since Compound A is relatively soluble in water-immiscible solvents (e.g. xylene) ordinarily employed for emulsifiable concentrate at room temperature, an emulsifiable concentrate comprising Compound A in a concentration of 10 to 15% by weight can be easily produced. However, the solubility of Compound A in such solvents at low temperatures (e.g. 0° C.) is small, and the storage stability at low temperatures is bad. Thus, Compound A tends to be crystallized out from its emulsifiable concentrate when stored at low temperatures. Because of this reason, a practically available emulsifiable concentrate contains Compound A only in a concentration of about 10% by weight or less. Instead of or in addition to the said ordinary water-immiscible solvents, the use of other water-soluble solvents which can well dissolve Compound A such as dimethylformamide or dimethylsulfoxide may be attempted.

Even from an aqueous dilution of such emulsifiable concentrate, Compound A is crystallized out within a short period of time. This crystallization causes unfavorably the clogging at the openings of the nozzle of a sprayer and further results in deterioration of the herbicidal activity. Thus, the appearance of an emulsifiable concentrate comprising Compound A in a high concentration and still having a high emulsion stability and a storage stability at low temperatures has been highly demanded.

As the result of an extensive study, it has now been found that the use of a certain solvent mixture can provide an emulsifiable concentrate comprising Compound A in a higher concentration with a higher emulsion stability and a storage stability at low temperatures in comparison with the sole use of each solvent component in the solvent mixture.

The emulsifiable concentrate of the present invention comprises 10 to 20 parts by weight of N'-[4-(4-methylphenethyloxy)phenyl]-N-methoxy-N-methylurea, 5 to 15 parts by weight of an emulsifier, 10 to 70 parts by weight of at least one of aromatic hydrocarbon solvents of the formula:

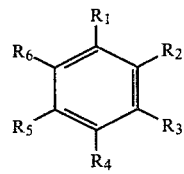

wherein $R_1$, $R_2$, $R_3$, $R_4$, $R_5$ and $R_6$ are each hydrogen or alkyl having 1 to 3 carbon atoms and 15 to 75 parts by weight of at least one of ketonic solvents having not more than 9 carbon atoms, of which the water solubility is not more than 10% by weight at room temperature.

Examples of the aromatic hydrocarbon solvent are benzene, toluene, xylene, methylethylbenzene, trimethylbenzene, tetramethylbenzene, dimethylethylbenzene, trimethylethylbenzene, dimethylpropylbenzene, diethylmethylbenzene, ethylpropylbenzene, etc. These aromatic hydrocarbon solvents may be used in mixture. For instance, "Solvesso 100" (manufactured by Esso Standard Co.), "Solvesso 150" (manufactured by Esso Standard Co.), "Shellsol A" (manufactured by Shell Oil Co.), "Tenneco 500/100" (manufactured by Tenneco Oil Co.), etc., which are commercially available mixtures of said aromatic hydrocarbon solvents, can be used as such in the emulsifiable concentrate of the invention.

Examples of the ketonic solvents are acetophenone, methylcyclohexanone, isophorone, methylisobutylketone, methyl-n-amylketone, ethyl-n-butylketone, etc. Ketonic solvents having a water solubility of more than 10% by weight (e.g. acetone, diacetone alcohol) are not usable, because the resultant emulsifiable concentrate is inferior in emulsion stability. Ketonic solvents having more than 9 carbon atoms (e.g. di-n-amylketone) are also not usable, because the resulting emulsifiable concentrate is inferior in solubility of Compound A therein.

The weight proportion of the aromatic hydrocarbon solvent(s) and the ketonic solvent(s) may be from 10:75 to 70:15, particularly 10:55 to 25:40. This weight proportion is largely varied with the concentration of Compound A.

As the emulsifier, there may be employed a mixture of at least one anionic surfactant and at least two nonionic surfactants. Examples of the anionic surfactant are sodium salts and calcium salts of alkylbenzenesulfonates. The use of calcium alkylbenzenesulfonates is particularly preferred. Examples of the non-ionic surfactant are polyoxyethylene alkyl ether, polyoxyethylene alkyl aryl ether, polyoxyethylene styryl aryl ether, polyoxyethylene styryl aryl ether polymer, polyoxyethylene fatty acid ester, oxyethylene oxypropylene polymer, etc. The surfactants which are suitable for this invention are commercially available under the trade names "Sorpol 2680" (manufactured by Toho Kagaku K.K.), "Sorpol 1200" (manufactured by Toho Kagaku K.K.), "Sorpol 3005X" (manufactured by Toho Kagaku K.K.), "Sorpol 355" (manufactured by Toho Kagaku K.K.), "Hymal PS10A" (manufactured by Matsumoto Yushi K.K.), etc.

Practical and presently preferred embodiments of the present invention are illustratively shown in the following Examples wherein part(s) and % are by weight.

EXAMPLE 1

Compound A (20 parts), Sorpol 2680 (a surfactant manufactured by Toho Kagaku K.K.; 15 parts), xylene (20 parts) and isophorone (45 parts) were mixed together to make an emulsifiable concentrate comprising Compound A in a concentration of 20%.

EXAMPLE 2

Compound A (10 parts), Sorpol 2680 (5 parts), xylene (70 parts) and isophorone (15 parts) were mixed together to make an emulsifiable concentrate comprising Compound A in a concentration of 10%.

EXAMPLE 3

Compound A (20 parts), Sorpol 2680 (15 parts), Solvesso 150 (a solvent manufactured by Esso Standard Co.; 15 parts) and isophorone (50 parts) were mixed together to make an emulsifiable concentrate comprising Compound A in a concentration of 20%.

EXAMPLE 4

Compound A (20 parts), Sorpol 2680 (15 parts), xylene (20 parts) and methylcyclohexanone (45 parts) were mixed together to make an emulsifiable concentrate comprising Compound A in a concentration of 20%.

EXAMPLE 5

Compound A (20 parts), Sorpol 2680 (15 parts), Shellsol A (a solvent manufactured by Shell Oil Co.; 20 parts) and methylisobutylketone (45 parts) were mixed together to make an emulsifiable concentrate comprising Compound A in a concentration of 20%.

EXAMPLE 6

Compound A (20 parts), Sorpol 1200 (15 parts), xylene (10 parts) and isophorone (55 parts) were mixed together to make an emulsifiable concentrate comprising Compound A in a concentration of 20%.

Comparative Example 1

Compound A (10 parts), Sorpol 2680 (15 parts) and xylene (75 parts) were mixed together to make an emulsifiable concentrate comprising Compound A in a concentration of 10%.

Comparative Example 2

Compound A (20 parts), Sorpol 2680 (15 parts) and isophorone (65 parts) were mixed together to make an emulsifiable concentrate comprising Compound A in a concentration of 20%.

Comparative Example 3

Compound A (20 parts), Sorpol 2680 (16 parts), xylene (16 parts) and diacetone alcohol (48 parts) were mixed together to make an emulsifiable concentrate comprising Compound A in a concentration of 20%. (This emulsifiable concentrate corresponds to the composition as disclosed in Example of U.S. Pat. No. 3,119,682 (1964).)

Comparative Example 4

Compound A (20 parts), Sorpol 2680 (15 parts), xylene (20 parts) and dimethylformamide (45 parts) were mixed together to make an emulsifiable concentrate comprising Compound A in a concentration of 20%.

Comparative Example 5

Compound A (20 parts), Sorpol 2680 (15 parts), xylene (20 parts) and dimethylsulfoxide (45 parts) were mixed together to make an emulsifiable concentrate comprising Compound A in a concentration of 20%.

Test Example 1

Each of the emulsifiable concentrate prepared in Examples 1 to 6 and Comparative Examples 1 to 5 was kept in an incubator of 0° C., and the precipitation of crystals was observed macroscopically.

The results are shown in Table 1.

TABLE 1

|  | After 1 day | After 2 days | After 3 days | After 7 days |
|---|---|---|---|---|
| Example 1 | − | − | − | − |
| 2 | − | − | − | − |
| 3 | − | − | − | − |
| 4 | − | − | − | − |
| 5 | − | − | − | − |
| 6 | − | − | − | − |
| Comparative Example 1 | + | + | + | + |
| 2 | − | − | − | − |
| 3 | − | − | − | − |
| 4 | − | − | − | − |
| 5 | − | − | − | − |

+, precipitated crystals observed;
−, precipitated crystals not observed.

Test Example 2

Each of the emulsifiable concentrate prepared in Examples 1 to 6 and Comparative Examples 1 to 5 was diluted with WHO standard hard water to make a dilution comprising Compound A in a concentration of 1000 ppm at 30° C., and the emulsion stability was observed macroscopically.

The results are shown in Table 2.

TABLE 2

|  | After 30 minutes | After 60 minutes | After 120 minutes |
|---|---|---|---|
| Example 1 | A | A | B |
| 2 | A | A | A |
| 3 | A | A | B |
| 4 | A | A | B |
| 5 | A | A | B |
| 6 | A | A | B |
| Comparative Example 1 | A | A | A |
| 2 | D | E | E |
| 3 | D | E | E |
| 4 | D | E | E |

TABLE 2-continued

| | After 30 minutes | After 60 minutes | After 120 minutes |
|---|---|---|---|
| 5 | D | E | E |

Note:
A. stable; B. precipitated crystals extremely trace; C. precipitated crystals trace; D. precipitated crystals small; E. precipitated crystals considerable.

Test Example 3

Into a plastic tray of 35 cm×25 cm×10 cm (high), field soil was filled, and the seeds of soybean, morningglory (*Ipomoea purpurea*), cocklebur (*Xanthium chinese*), velvetleaf (*Abutilon theophrasti*), large crabgrass (*Digitaria sanguinalis*) and barnyard grass (*Echinochloa crus-galli*) were sowed and cultivated in a greenhouse for 3 weeks. A designed amount of the emulsifiable concentrate as prepared in Example 1 or 4 and a wettable powder was diluted with water to make a volume of 5 liters per are, and the dilution was applied over the top of the plants by the aid of a small sprayer for foliar treatment. After cultivation in the greenhouse for additional 3 weeks, the remaining terrestrial parts of the plants was measured, and the percentage of the measured weight in the treated plot to the measured weight in the untreated plot was calculated. The phytotoxicity and the herbicidal activity were evaluated on the following criteria:

| Evaluated value | Fresh weight (percentage to untreated plot) | |
|---|---|---|
| | Soybean | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The results are shown in Table 3.

TABLE 3

| | Dose of Compound A (g/are) | Soybean | Weeds | | | | |
|---|---|---|---|---|---|---|---|
| | | | Morningglory | Cocklebur | Velvetleaf | Large crabgrass | Barnyard grass |
| Example 1 | 10 | 0 | 5 | 5 | 5 | 5 | 4 |
| | 5 | 0 | 5 | 5 | 5 | 4 | 4 |
| | 2.5 | 0 | 4 | 5 | 4 | 3 | 3 |
| Example 4 | 10 | 0 | 5 | 5 | 5 | 5 | 5 |
| | 5 | 0 | 5 | 5 | 5 | 4 | 4 |
| | 2.5 | 0 | 4 | 5 | 5 | 4 | 3 |
| Wettable powder | 10 | 0 | 5 | 5 | 5 | 3 | 2 |
| | 5 | 0 | 4 | 5 | 5 | 2 | 1 |
| | 2.5 | 0 | 3 | 4 | 4 | 1 | 0 |

Test Example 4

Into a plastic tray of 35 cm×25 cm×10 cm (high), field soil was filled, and the seeds of soybean, morningglory (*Ipomoea purpurea*), cocklebur (*Xanthium chinese*) and sicklepod (*Cassia tora*) were sowed and cultivated in a greenhouse for 3 weeks. A designed amount of the emulsifiable concentrate as prepared in Examples 1 to 3 or Comparative Examples 2 to 4 was diluted with water to make a volume of 5 liters per are. The dilution was applied over the top of the plants by the aid of a small sprayer for foliar treatment. After cultivation in the greenhouse for additional 3 weeks, the fresh weight of the remaining terrestrial part of the plants was measured, and the percentage of the measured weight in the treated plot to the measured weight in the untreated plit was calculated. The phytotoxicity and the herbicidal activity were evaluated on the criteria as shown in Test Example 3.

The results are shown in Table 4.

TABLE 4

| | Dose of Compound A (g/are) | Soybean | Weeds | | |
|---|---|---|---|---|---|
| | | | Morningglory | Cocklebur | Sicklepod |
| Example 1 | 10 | 0 | 5 | 5 | 5 |
| | 5 | 0 | 5 | 5 | 4 |
| | 2.5 | 0 | 4 | 5 | 3 |
| Example 2 | 10 | 0 | 5 | 5 | 5 |
| | 5 | 0 | 5 | 5 | 4 |
| | 2.5 | 0 | 5 | 5 | 3 |
| Example 3 | 10 | 0 | 5 | 5 | 5 |
| | 5 | 0 | 5 | 5 | 4 |
| | 2.5 | 0 | 4 | 5 | 4 |
| Comparative Example 2 | 10 | 0 | 4 | 5 | 4 |
| | 5 | 0 | 3 | 5 | 3 |
| | 2.5 | 0 | 3 | 3 | 1 |
| Comparative Example 3 | 10 | 0 | 4 | 5 | 4 |
| | 5 | 0 | 3 | 5 | 2 |
| | 2.5 | 0 | 2 | 3 | 1 |
| Comparative Example 4 | 10 | 0 | 4 | 5 | 4 |
| | 5 | 0 | 3 | 4 | 3 |
| | 2.5 | 0 | 3 | 3 | 1 |

As understood from Test Example 1, the sole use of the aromatic hydrocarbon solvent is insufficient in the storage stability at low temperatures. As understood from Test Example 2, the sole use of the ketonic solvent is unsatisfactory in the emulsion stability. Only the combined use of the aromatic hydrocarbon solvent and the ketonic solvent can give an emulsifiable concentrate, which is satisfactory in the storage stability at low temperatures and the emulsion stability.

What is claimed is:

1. An emulsifiable concentrate for weed control, consisting essentially of 10 to 20 parts by weight of N'-[4-(4-methylphenethyloxy)phenyl]-N-methoxy-N-methylurea, 5 to 15 parts by weight of an emulsifier, 10 to 70 parts by weight of at least one aromatic hydrocarbon solvent of the formula:

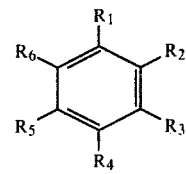

wherein $R_1$, $R_2$, $R_3$, $R_4$, $R_5$ and $R_6$ are each hydrogen or alkyl having 1 to 3 carbon atoms and 15 to 75 parts by weight of at least one ketonic solvent having not more than 9 carbon atoms and having a water solubility of not more than 10% by weight at room temperature, said emulsifier being a mixture of at least one anionic surfactant selected from the group consisting of the calcium or sodium salt of an alkylbenzenesulfonic acid and at least two non-ionic surfactants selected from the group consisting of polyoxyethylene alkyl ether, polyoxyethylene alkyl aryl ether, polyoxyethylene styryl aryl ether, polyoxyethylene styryl aryl ether polymer, polyoxyethylene fatty acid ester, oxyethylene oxypropylene polymer, and mixtures thereof.

2. The emulsifiable concentrate according to claim 1, wherein said aromatic hydrocarbon solvent is selected from the group consisting of benzene, toluene, xylene, methylethylbenzene, trimethylbenzene, tetramethylbenzene, dimethylethylbenzene, trimethylethylbenzene, dimethylpropylbenzene, diethylmethylbenzene and ethylpropylbenzene, and mixtures thereof.

3. The emulsifiable concentrate according to claim 1, wherein said ketonic solvent is selected from the group consisting of acetophenone, methylcyclohexanone, isophorone, methylisobutylketone, methyl-n-amylketone and ethyl-n-butylketone, and mixtures thereof.

4. The emulsifiable concentrate according to claim 1, wherein the weight proportion of said aromatic hydrocarbon solvent and said ketonic solvent is from 10:75 to 70:15.

5. The emulsifiable concentrate according to claim 4, wherein the weight proportion of said aromatic hydrocarbon solvent and said ketonic solvent is from 10:55 to 25:40.

6. A method of selectively combating weeds in the cultivation of soybean, peanut, cotton, corn, wheat or rice, which comprises applying a herbicidally effective amount of the composition according to claim 1 to the area where the soybean, peanut, cotton, corn, wheat or rice is cultivated.

* * * * *